(12) United States Patent
De La Mettrie

(10) Patent No.: US 7,608,115 B2
(45) Date of Patent: Oct. 27, 2009

(54) PROCESS FOR TREATING KERATIN FIBRES BY APPLYING HEAT

(75) Inventor: Roland De La Mettrie, Le Vésinet (FR)

(73) Assignee: L'Oreal S.A., Paris (FR)

( * ) Notice: Subject to any disclaimer, the term of this patent is extended or adjusted under 35 U.S.C. 154(b) by 25 days.

(21) Appl. No.: 10/556,044

(22) PCT Filed: Apr. 30, 2004

(86) PCT No.: PCT/EP2004/006058

§ 371 (c)(1),
(2), (4) Date: Jan. 26, 2007

(87) PCT Pub. No.: WO2004/098550

PCT Pub. Date: Nov. 18, 2004

(65) Prior Publication Data

US 2007/0174974 A1    Aug. 2, 2007

Related U.S. Application Data

(60) Provisional application No. 60/513,577, filed on Oct. 24, 2003.

(30) Foreign Application Priority Data

May 9, 2003    (FR)    ................... 03 05636

(51) Int. Cl.
*A61Q 5/10*    (2006.01)

(52) U.S. Cl. ................ 8/405; 8/406; 8/407; 8/435; 8/463; 8/552; 8/557; 8/558

(58) Field of Classification Search .......... 8/405, 8/406, 407, 435, 463, 552, 557, 558; 132/202, 132/208

See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,874,870 A | 4/1975 | Green et al. | |
| 3,912,808 A | 10/1975 | Sokol | |
| 3,917,817 A | 11/1975 | Valerberghe et al. | |
| 3,926,891 A | 12/1975 | Gross et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,103,145 A | 7/1978 | Oliveri | |
| 4,131,576 A | 12/1978 | Iovine et al. | |
| 4,165,367 A | 8/1979 | Chakrabarti | |
| 4,172,887 A | 10/1979 | Vanlerberghe et al. | |
| 4,189,468 A | 2/1980 | Vanlerberghe et al. | |
| 4,190,562 A | 2/1980 | Westerman | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,293,609 A | 10/1981 | Erickson | |

(Continued)

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| EP | 0 080 976 | 6/1983 |
| EP | 0 122 324 A1 | 10/1984 |

(Continued)

OTHER PUBLICATIONS

English Abstract of the Japanese Patent No. JP 05051309 A (1993).*
STIC Search Report Dated Jul. 8, 2008.*
International Search Report for PCT/EP2004/006058, dated Sep. 10, 2004.
English language abstract of EP 0 080 976 A1, Jun. 8, 1983.
English language abstract of EP 0 770 375 A1, May 2, 1997.
English language abstract of JP 2-19576, Jan. 23, 1990.
English language abstract of JP 5-163124, Jun. 29, 1993.
English language abstract of JP 58-99408, Jun. 13, 1983.
English language abstract of JP 61-10502, Jan. 18, 1986.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present invention relates to a process for treating keratin fibers, which comprises the application to the keratin fibers of a hair composition comprising at least one active agent chosen from hair dyes, oxidizing agents and cationic conditioners, followed by the application to the fibers of a heating iron whose temperature is greater than or equal to 60° C. The invention also relates to a composition comprising at least one superabsorbent polymer and at least-one active agent chosen from hair dyes, oxidizing agents and cationic conditioners.

19 Claims, No Drawings

U.S. PATENT DOCUMENTS

| | | | |
|---|---|---|---|
| 4,308,878 | A | 1/1982 | Silva |
| 4,349,532 | A | 9/1982 | Vanlerberghe et al. |
| 4,422,853 | A | 12/1983 | Jacquet et al. |
| 4,424,247 | A | 1/1984 | Erickson |
| 4,535,098 | A | 8/1985 | Evani et al. |
| 4,591,610 | A | 5/1986 | Grollier |
| 4,608,250 | A | 8/1986 | Jacquet et al. |
| 4,761,273 | A | 8/1988 | Grollier et al. |
| 4,839,166 | A | 6/1989 | Grollier et al. |
| 4,948,579 | A | 8/1990 | Jacquet et al. |
| 4,996,059 | A | 2/1991 | Grollier et al. |
| 5,061,289 | A | 10/1991 | Clausen et al. |
| 5,089,252 | A | 2/1992 | Grollier et al. |
| 5,139,037 | A | 8/1992 | Grollier et al. |
| 5,196,189 | A | 3/1993 | Jacquet et al. |
| 5,380,340 | A | 1/1995 | Neunhoeffer et al. |
| 5,494,058 | A | 2/1996 | Chan |
| 5,520,706 | A | 5/1996 | Samain et al. |
| 5,534,267 | A | 7/1996 | Neunhoeffer et al. |
| 5,663,366 | A | 9/1997 | Neunhoeffer et al. |
| 5,685,882 | A | 11/1997 | Samain et al. |
| 5,708,151 | A | 1/1998 | Möckli |
| 5,711,765 | A | 1/1998 | Audousset |
| 5,766,576 | A | 6/1998 | Löwe et al. |
| 5,957,140 | A | 9/1999 | McGee |
| 5,983,903 | A | 11/1999 | Nanba et al. |
| 6,056,946 | A | 5/2000 | Crudele et al. |
| 6,073,635 | A | 6/2000 | Todd |
| 6,099,592 | A | 8/2000 | Vidal et al. |
| 6,284,003 | B1 | 9/2001 | Rose et al. |
| 6,338,741 | B1 | 1/2002 | Vidal et al. |
| 6,645,258 | B2 | 11/2003 | Vidal et al. |
| 6,660,045 | B1 * | 12/2003 | Hoeffkes et al. ............... 8/405 |
| 6,730,789 | B1 | 5/2004 | Birault et al. |
| 2002/0050013 | A1 | 5/2002 | Vidal et al. |
| 2002/0061321 | A1 | 5/2002 | Bara |
| 2003/0019051 | A9 | 1/2003 | Vidal et al. |

FOREIGN PATENT DOCUMENTS

| | | | |
|---|---|---|---|
| EP | 0 337 354 | A1 | 10/1989 |
| EP | 0 503 507 | A1 | 9/1992 |
| EP | 0 714 954 | A2 | 6/1996 |
| EP | 0 770 375 | A1 | 5/1997 |
| FR | 1 492 597 | | 8/1967 |
| FR | 1 583 363 | | 10/1969 |
| FR | 2 077 143 | | 10/1971 |
| FR | 2 080 759 | | 11/1971 |
| FR | 2 162 025 | | 7/1973 |
| FR | 2 190 406 | | 2/1974 |
| FR | 2 252 840 | | 6/1975 |
| FR | 2 270 846 | | 12/1975 |
| FR | 2 280 361 | | 2/1976 |
| FR | 2 316 271 | | 1/1977 |
| FR | 2 320 330 | | 3/1977 |
| FR | 2 336 434 | | 7/1977 |
| FR | 2 368 508 | | 5/1978 |
| FR | 2 383 660 | | 10/1978 |
| FR | 2 393 573 | | 1/1979 |
| FR | 2 413 907 | | 8/1979 |
| FR | 2 470 596 | | 6/1981 |
| FR | 2 505 348 | | 11/1982 |
| FR | 2 519 863 | | 7/1983 |
| FR | 2 542 997 | A1 | 9/1984 |
| FR | 2 598 611 | A1 | 11/1987 |
| FR | 2 733 749 | A1 | 11/1996 |
| FR | 2 801 308 | A1 | 5/2001 |
| GB | 1 026 978 | | 4/1966 |
| GB | 1 153 196 | | 5/1969 |
| GB | 1 331 819 | | 9/1973 |
| GB | 1 347 051 | | 2/1974 |
| GB | 1 479 786 | | 7/1977 |
| GB | 1 546 809 | | 5/1979 |
| JP | 58-99408 | | 6/1983 |
| JP | 61-10502 | | 1/1986 |
| JP | 2-19576 | | 1/1990 |
| JP | 4-282307 | | 10/1992 |
| JP | 5-163124 | | 6/1993 |
| JP | 7-324018 | | 12/1995 |
| JP | 8-40856 | | 2/1996 |
| JP | 8-99843 | | 4/1996 |
| JP | 2000-302647 | | 10/2000 |
| JP | 2000-302648 | | 10/2000 |
| JP | 2001-213741 | | 8/2001 |
| JP | 2002-121109 | | 4/2002 |
| JP | 2002-138022 | | 5/2002 |
| JP | 2002-265339 | | 9/2002 |
| WO | WO 94/08969 | | 4/1994 |
| WO | WO 94/08970 | | 4/1994 |
| WO | WO 95/01772 | | 1/1995 |
| WO | WO 95/15144 | | 6/1995 |
| WO | WO 96/15765 | | 5/1996 |
| WO | WO 99/29285 | * | 6/1999 |
| WO | WO 02/078655 | A2 | 10/2002 |

OTHER PUBLICATIONS

English language abstract of JP 2000-302647, Oct. 31, 2000.
English language abstract of JP 2000-302648, Oct. 31, 2000.
English language abstract of JP 2001-213741, Aug. 7, 2001.
English language abstract of JP 2002-138022, May 14, 2002.
English language abstract of JP 2002-265339, Sep. 18, 2002.

* cited by examiner

PROCESS FOR TREATING KERATIN FIBRES BY APPLYING HEAT

CROSS REFERENCE TO RELATED APPLICATIONS

This application claims the right to priority based on French Application No. 0305636, filed May 9, 2003, and claims the benefit of U.S. Provisional Application No. 60/513,577, filed Oct. 24, 2003, the content of both of which is incorporated herein by reference in its entirety.

The present invention relates to a novel process for treating keratin fibres by applying heat. Such a process allows more pronounced results to be obtained.

It is known practice to dye keratin fibres, and in particular human hair, with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds by a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

It is also known practice to dye keratin fibres by direct dyeing. The process conventionally used in direct dyeing consists in applying to the keratin fibres direct dyes, which are coloured molecules and dyes that have an affinity for the fibres, in leaving these agents to act and then in optionally rinsing the fibres. The direct dyes may be chosen especially from dyes of the nitrobenzene, anthraquinone, nitropyridine, azo, xanthine, acridine or azine type, or methine dyes. These direct dyes may be of nonionic, anionic or cationic nature.

The colorations resulting therefrom are particularly chromatic but are, however, temporary or semi-permanent since the nature of the interactions which bind the direct dyes to the keratin fibre, and their desorption from the surface and/or from the core of the fibre, are responsible for their poor dyeing power, their lack of chromaticity and their poor wash-fastness or perspiration-fastness.

It is also known practice to use oxidizing agents to treat the hair, in particular in the case of the oxidation dyeing described above and in the case of permanently reshaping, bleaching or stripping the hair.

In the case of permanently reshaping (permanent-waving or relaxing) the hair, the oxidizing agent is used in fixing compositions that allow the hair to be fixed in the desired shape once the disulphide bonds of the hair have been broken using a reducing compound.

In the case of bleaching or stripping, the oxidizing agent is used to destroy the dyes present in the hair, whether they are melanin pigments in the case of bleaching naturally pigmented hair, or synthetic dyes in the case of dyed hair.

In any case, there is a need to increase the efficacy of the process concerned without increasing the concentrations of oxidizing agents, so as not to harm the integrity of the hair.

Finally, it is known practice to use cationic agents to condition the hair, i.e. to improve its cosmetic properties and in particular the softness or the ease of disentangling. This is particularly important when the treatment applied to the hair induces a risk of impairing the hair, for example dyeing, permanent-reshaping or bleaching treatments, or when these treatments are applied to hair that is already sensitized.

There is in this case also a need to increase the efficacy of these cationic agents without increasing their concentration, since these products are often sparingly degradable and the amount thereof in wastewater should thus be limited.

One of the aims of the present invention is to provide a novel process for treating keratin fibres more quickly and more efficiently.

One of the particular aims of the invention is to provide a process for treating keratin fibres that can in particular produce more intense colorations quickly and simply.

This aim is achieved by the present invention, one subject of which is a process for treating keratin fibres that comprises the application to the keratin fibres of a hair composition comprising, in a medium that is suitable for dyeing fibres, at least one active agent chosen from direct dyes, oxidation bases, couplers and oxidizing agents, followed by a step of heating the fibres coated with the hair composition, using a heating iron whose temperature is greater than or equal to 60° C.

It is thus possible to obtain faster and longer-lasting treatments, for example treatments that show better resistance to water and shampoo.

According to one embodiment, the process is preferably a process for dyeing keratin fibres in which the hair composition comprises at least one active agent chosen from direct dyes, oxidation bases and couplers and at least one oxidizing agent.

Hair dyes such as direct dyes, oxidation bases and couplers may be compounds that are conventionally synthesized or extracted from plant or animal species, this extract being obtained from the whole organism or a part thereof, for example using the leaves or the roots. The active substances that may be extracted from plant species are, for example, hydroxylated quinones, indigoids, hydroxyflavones, the A and B santalins, isatin and its derivatives, and brasilin and its hydroxylated derivative. The plant species that may be used in the present invention are for example, henna, indigo plant, camomile, annatto and alkanet. The animal species that may be used are, for example, cochineals.

The oxidation bases are generally chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis-(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylene-diamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diamino-phenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol, 4-amino-2-chloro-phenol, 4-amino-2,6-dichlorophenol, 4-amino 6-[(5'-amino 2'-hydroxy 3'-methylphenyl)methyl]2-methylphenol and bis-(5-amino 2-hydroxyphenyl)methane and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention include the 3-amino-pyrazolo[1,5-a]pyridine oxidation bases or the addition salts thereof described, for example, in patent application FR 2 801 308; By way of example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-amino-pyrazolo[1,5-a]pyrid-7-yl)methanol; 2-(-3-aminopyrazolo-[1,5-a]pyrid-5-yl)ethanol; 2-(3-aminopyrazolo[1,5-a]-pyrid-7-yl)ethanol; (3-aminopyrazolo[1,5-a]pyrid-2-yl)-methanol; 3,6-diaminopyrazolo[1,5-a]pyridine; 3,4-diaminopyrazolo[1,5-a]pyridine; pyrazolo[1,5-a]-pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)-amino]ethanol; 2-[(3-aminopyrazolo[1,5-a]pyrid-7-yl)-(2-hydroxyethyl)amino]ethanol; 3-aminopyrazolo[1,5-a]-pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the addition salts thereof with an acid or with a base.

Among the pyrimidine derivatives that can be mentioned are the compounds described, for example, in patents DE 2 359 399; JP 88-169 571; JP 05-63124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo [1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo-[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]-pyrimidine-3,7-diamine, 2,5,N7,N7-tetramethylpyrazolo-[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives that may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenyl-pyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The couplers that are useful in the context of the present invention are, for example, meta-phenylenediamine, meta-aminophenol, meta-diphenol, naphthalene-based and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hyroxyethylamino)-1-methoxybenzene, 1,3-diamino-benzene, 1,3-bis(2,4-diaminophenoxy)propane, 3-ureido-aniline, 3-ureido-1-dimethylaminobenzene, sesamol, 1-β-hydroxyethylamino-3, 4-methylenedioxybenzene, α-naphthol, 2-methyl-1- naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene and 2,6-bis(β-hydroxy-ethylamino)toluene and the addition salts thereof with an acid.

In general, the addition salts of the oxidation bases and of the couplers that may be used in the context of the invention are chosen especially from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, ammonia, amines or alkanolamines.

The direct dyes that may be used according to the invention are preferably chosen from neutral, acidic or cationic nitrobenzene direct dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes.

Among the benzenic direct dyes that may be used according to the invention, mention may be made, in a non-limiting manner, of the following compounds:
1,4-diamino-2-nitrobenzene
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis-(β-hydroxyethylamino)benzene
1-β-hydroxyethylamino-2-nitro-4-aminobenzene
1-β-hydroxyethylamino-2-nitro-4-(ethyl)(β-hydroxy-ethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-[bis(β-hydroxyethyl)amino]-3-nitrobenzene
1-β-hydroxyethylamino-2-nitrobenzene
1-hydroxy-4-β-hydroxyethylamino-3-nitrobenzene.

Among the azo direct dyes, mention may be made of the cationic azo dyes described in patent applications WO 95/115144, WO 95/01772 and EP 714 954, the content of which forms an integral part of the invention.

Among these compounds, mention may be made most particularly of the following dyes: 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]pyridinium methyl sulphate.

Among the azo direct dyes that may also be mentioned are the following dyes described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-amino-diphenylazo)-2-methyl-4-[bis(β-hydroxyethyl)-amino]benzene and 4-hydroxy-3-(2-methoxyphenylazo)-1-naphthalenesulphonic acid.

Among the quinone direct dyes that may be mentioned are the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-amino-propylaminoanthraquinone, 5-β-hydroxyethyl-1,4-diaminoanthraquinone, 2-aminoethylaminoanthraquinone, 1,4-bis (β,γ-dihydroxypropylamino)anthraquinone.

Among the azine dyes that may be mentioned are the following compounds: Basic Blue 17, Basic Red 2.

Among the triarylmethane dyes that may be used according to the invention, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds:
2-β-hydroxyethylamino-5-[bis(β-4'-hydroxyethyl)amino]-anilino-1,4-benzoquinone;.
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The amount of oxidation bases present in the dye composition obtained by the process of the present invention is generally between 0.001% and 10% by weight and preferably between 0.005% and 6% by weight approximately relative to the total weight of the dye composition.

The amount of couplers present in the dye composition obtained by the process of the present invention is generally between 0.001% and 10% by weight and preferably between 0.005% and 6% by weight approximately relative to the total weight of the dye composition.

The amount of direct dyes present in the dye composition obtained by the process of the present invention is generally between 0.001% and 20% by weight approximately and even more preferably between 0.005% and 10% by weight approximately relative to the total weight of the ready-to-use composition.

The oxidizing agents that are useful in the context of the present invention are the oxidizing agents conventionally used in the field of hair treatment. Such oxidizing agents are, for example, hydrogen peroxide, urea peroxide, alkali metal bromates, persalts such as perborates and persulphates, peracids and oxidase enzymes, among which mention may be made of peroxidases, 2-electron oxidoreductases such as uricases and 4-electron oxygenases, for instance laccases. Hydrogen peroxide is particularly preferred.

The cationic conditioners that are useful in the present invention are conditioners that are conventional in the field of hair treatment. Such agents are, for example, cationic monomers or cationic polymers.

The cationic conditioners of polymeric type that may be used in accordance with the present invention may be chosen from all those already known per se as improving the cosmetic properties of hair treated with detergent compositions, i.e. especially those described in patent application EP-A-0 337 354 and in French patent applications FR-A-2 270 846, 2 383 660, 2 598 611, 2 470 596 and 2 519 863.

Even more generally, for the purposes of the present invention; the term "cationic polymers" denotes any polymer comprising cationic groups and/or groups that may be ionized into cationic groups.

The cationic polymers that are preferred are chosen from those containing units comprising primary, secondary, tertiary and/or quaternary amine groups that either may form part of the main polymer chain or may be borne by a side substituent directly attached thereto.

The cationic polymers used generally have a number average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type. These are known products.

The polymers of the polyamine, polyamino amide and polyquaternary ammonium type that pay be used in accordance with the present invention, and that may especially be mentioned, are those described in French patents Nos 2 505 348 and 2 542 997. Among these polymers, mention may be made of:

(1) homopolymers or copolymers derived from acrylic or methacrylic esters or amides and comprising at least one of the units of the following formulae:

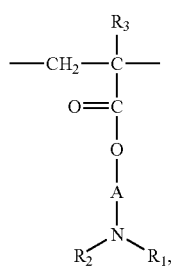

(XII)

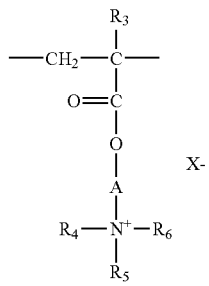

(XIII)

-continued

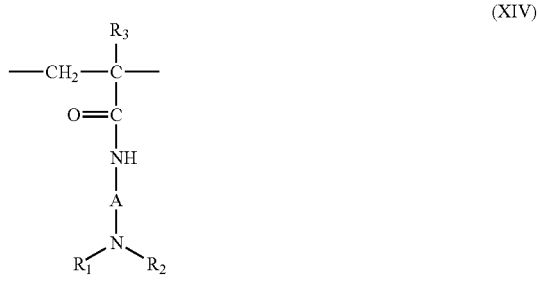

(XIV)

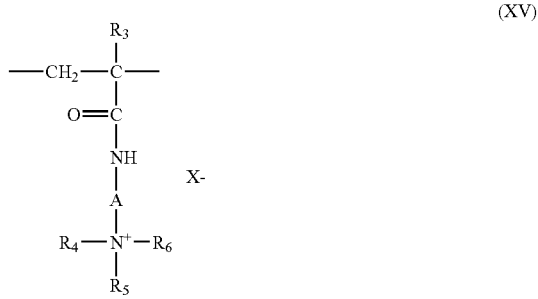

(XV)

in which:
$R_1$ and $R_2$, which may be identical or different, represent hydrogen or an alkyl group containing from 1 to 6 carbon atoms, and preferably methyl or ethyl;
$R_3$, which may be identical or different, denote a hydrogen atom or a $CH_3$ radical;
A, which may be identical or different, represent a linear or branched alkyl group of 1 to 6 carbon atoms, preferably 2 or 3 carbon atoms, or a hydroxyalkyl group of 1 to 4 carbon atoms;
$R_4$, $R_5$, $R_6$, which may be identical or different, represent an alkyl group containing from 1 to 18 carbon atoms or a benzyl radical and preferably an alkyl group containing from 1 to 6 carbon atoms;
X denotes an anion derived from a mineral or organic acid, such as a methyl sulphate anion or a halide such as chloride or bromide.

The copolymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these copolymers of family (1), mention may be made of:
copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba, the copolymer of acrylamide and of methacryloyloxyethyltrimethylammonium methosulphate sold under the name Reten by the company Hercules, quaternized or nonquaternized vinylpyrrolidone/dialkylaminoalkyl acrylate or methacrylate copolymers, such as the products sold under the name "Gafquat" by the company ISP, such as, for example, "Gafquat® 734" or "Gafquat® 755", or alternatively the products known as "Copolymer 845, 958 and 937". These polymers are described in detail in French patents 2 077 143 and 2 393 573.

dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold in particular under the name Styleze® CC 10 by ISP, quaternized vinylpyrrolidone/dimethylaminopropylmethacrylamide copolymers, such as the product sold under the name "Gafquat® HS 100" by the company ISP.

(2) cationic polysaccharides, especially cationic celluloses and cationic galactomannan gums. Among the cationic polysaccharides that may be mentioned more particularly are cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups, which are described in French patent 1 492 597 and in particular the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described especially in U.S. Pat. No. 4,131,576, such as hydroxyalkylcelluloses, for instance hydroxymethyl-, hydroxyethyl- or hydroxypropylcelluloses grafted especially with a methacryloylethyltrimethylammonium, methacrylamidopropyltrimethylammonium or dimethyl-diallylammonium salt.

The commercial products corresponding to this definition are more particularly the products sold under the names "Celquat® L 200" and "Celquat® H 100" by the company National Starch.

The cationic galactomannan gums are described more particularly in U.S. Pat. Nos. 3,589,578 and 4,031,307, in particular guar gums containing trialkyl-ammonium cationic groups. Use is made, for example, of guar gums modified with a salt (e.g. chloride) of 2,3-epoxypropyltrimethylammonium.

Such products are sold especially under the trade names Jaguar® C13 S, Jaguar® C 15, Jaguar® C 17 or Jaguar® C162 by the company Meyhall.

(3) polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2 162 025 and 2 280 361.

(4) water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such, polymers are described, in particular, in French patents 2 252 840 and 2 368 508.

(5) polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylamino-hydroxypropyl/diethylenetriamine polymers sold under the name "Cartaretine® F, F4 or F8" by the company Sandoz.

(6) polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid being between 0.8:1 and 1.4:1; the polyamino amide resulting therefrom being reacted with epichlorohydrin in a molar ratio of epichlorohydrin, relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett® 57" by the company Hercules Inc. or alternatively under the names "PD 170" or "Delsette® 101" by the company Hercules in the case of the adipic acid/epoxypropyl/diethylenetriamine copolymer.

(7) cyclopolymers of alkyldiallylamine or of dialkyldiallylammonium, such as the homopolymers or copolymers containing, as main constituent of the chain, units corresponding to formula (XVI) or (XVII):

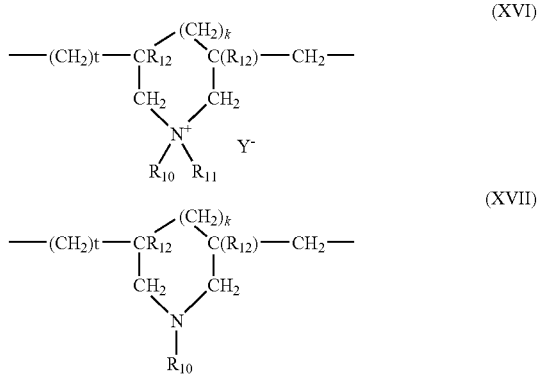

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group having from 1 to 8 carbon atoms, a hydroxyalkyl group in which the alkyl group preferably has 1 to 5 carbon atoms, a lower $C_1$-$C_4$ amidoalkyl group; or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2 080 759 and in its Certificate of Addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallyl-ammonium chloride homopolymer sold under the name "Merquat® 100" by the company Nalco (and its homologues of low weight-average molecular mass) and copolymers of diallyldimethylammonium chloride and of acrylamide, sold under the name "Merquat® 550".

(8) quaternary diammonium polymers containing repeating units corresponding to the formula:

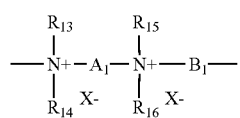

(XVIII)

in which formula (XVIII):

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second hetero atom other than nitrogen, or alternatively $R_{13}$, $R_{14}$, $R_{15}$ and $R_{16}$ represent a linear or branched $C_1$-$C_6$ alkyl radical substituted with a nitrile, ester, acyl or amide group or a group —CO—O—$R_{17}$-D or —CO—NH—$R_{17}$-D where $R_{17}$ is an alkylene and D is a quaternary ammonium group;

$A_1$ and $B_1$ represent polymethylene groups containing from 2 to 20 carbon atoms, which groups may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ denotes an anion derived from a mineral or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO-D-OC—$(CH_2)_n$— in which D denotes:

a) a glycol residue of formula: —O-Z-O—, where Z denotes a linear or branched hydrocarbon-based radical or a group corresponding to one of the following formulae:

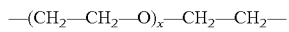

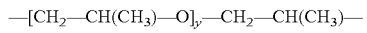

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

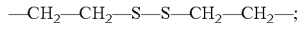

d) a ureylene group of formula: —NH—CO—NH—.

Preferably, $X^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the formula:

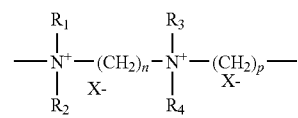

(XIX)

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

One compound of formula (XIX) which is particularly preferred is the one for which $R_1$, $R_2$, $R_3$ and $R_4$ represent a methyl radical and n=3, p=6 and X=Cl, which is known as Hexadimethrine chloride according to the INCI (CTFA) nomenclature.

(9) polyquaternary ammonium polymers consisting of units of formula (XX):

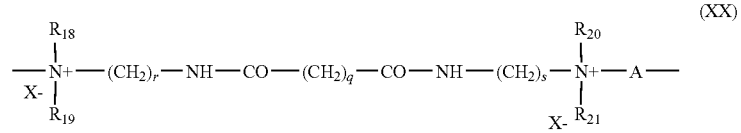

(XX)

in which formula:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_p$OH radical, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X⁻ denotes an anion such as a halide, A denotes a dihalide radical or preferably represents —CH₂—CH₂—O—CH₂—CH₂—.

Such compounds are described in particular in patent application EP-A-122 324.

Among these compounds, mention may be made, for example, of the products "Mirapol® A 15", "Mirapol® AD1", "Mirapol® AZ1" and "Mirapol® 175" sold by the company Miranol.

(10) quaternary polymers of vinylpyrrolidone and of vinylimidazole, for instance the products sold under the names Luviquat® FC 905, FC 550 and FC 370 by the company BASF.

(11) polyamines, for instance Polyquart® H sold by Cognis, referenced under the name Polyethylene Glycol (15) Tallow Polyamine in the CTFA dictionary.

(12) Crosslinked methacryloyloxy($C_1$-$C_4$) alkyltri-($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of the said copolymer in mineral oil can be used more particularly. This dispersion is sold under the name "Salcare® SC 92" by the company Ciba. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Ciba.

Other cationic polymers that can be used in the context of the invention are cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers that may be used in the context of the present invention, it is preferred to use quaternary cellulose ether derivatives such as the products sold under the name "JR 400" by the company Amerchol, cationic cyclopolymers, in particular the dimethyldiallylammonium chloride homopolymers or copolymers sold under the names "Merquat® 1000", "Merquat® 550" and "Merquat® S" by the company Nalco, quaternary polymers of vinylpyrrolidone and of vinylimidazole, and mixtures thereof.

The cationic proteins or protein hydrolysates are, in particular, chemically modified polypeptides bearing quaternary ammonium groups at the end of the chain or grafted thereto. Their molecular mass can range, for example, from 1500 to 10 000 and in particular from 2000 to 5000 approximately. Among these compounds, mention may be made in particular of:

collagen hydrolysates bearing triethylammonium groups, such as the products sold under the name "Quat-Pro E" by the company Maybrook and referred to in the CTFA dictionary as "Triethonium Hydrolyzed Collagen Ethosulphate";

collagen hydrolysates bearing trimethylammonium and trimethylstearylammonium chloride groups, sold under the name "Quat-Pro S" by the company Maybrook and referred to in the CTFA dictionary as "Steartrimonium Hydrolyzed Collagen";

animal protein hydrolysates bearing trimethylbenzylammonium groups such as the products sold under the name "Crotein® BTA" by the company Croda and referred to in the CTFA dictionary as "Benzyltrimonium hydrolyzed animal protein";

protein hydrolysates bearing, on the polypeptide chain, quaternary ammonium groups containing at least one alkyl radical having from 1 to 18 carbon atoms.

Among these protein hydrolysates, mention may be made of, inter alia:

"Croquat® L" in which the quaternary ammonium groups contain a $C_{12}$ alkyl group;

"Croquat® M" in which the quaternary ammonium groups contain $C_{10}$-$C_{18}$ alkyl groups;

"Croquat® S" in which the quaternary ammonium groups contain a $C_{18}$ alkyl group;

"Crotein® Q" in which the quaternary ammonium groups contain at least one alkyl group having from 1 to 18 carbon atoms.

These various products are sold by the company Croda.

Other quaternized proteins or hydrolysates are, for example, those corresponding to the formula:

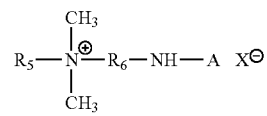

(XXI)

in which X⁻ is an anion of an organic or mineral acid, A denotes a protein residue derived from hydrolysates of a protein, especially of collagen, $R_5$ denotes a lipophilic group containing up to 30 carbon atoms and $R_6$ represents an alkylene group having 1 to 6 carbon atoms. Mention may be made, for example, of the products sold by the company Inolex under the name "Lexein® QX 3000", referred to in the CTFA dictionary as "Cocotrimonium Collagen Hydrolysate".

Mention may also be made of quaternized plant proteins such as wheat, corn or soybean proteins: as quaternized wheat proteins, mention may be made of those sold by the company Croda under the names "Hydrotriticum WQ or QM", referred to in the CTFA dictionary as "Cocodimonium Hydrolysed Wheat Protein", "Hydrotriticum QL", referred to in the CTFA dictionary as "Laurdimonium Hydrolysed Wheat Protein" or "Hydrotriticum QS", referred to in the CTFA dictionary as "Steardimonium Hydrolysed Wheat Protein".

The cationic surfactants are especially chosen from quaternary ammonium salts, quaternary ammonium salts of imidazoline, diquaternary ammonium salts, and quaternary ammonium salts containing at least one ester function.

The cationic surfactants may be chosen from:

A) the quaternary ammonium salts of general formula (XXII) below:

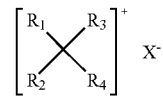

(XXII)

in which $X^-$ is an anion chosen from the group of halides (chloride, bromide or iodide) or ($C_2$-$C_6$)alkyl sulphates, more particularly methyl sulphate, phosphates, alkyl or alkylaryl sulphonates, anions derived from organic acid, such as acetate or lactate, and i) the radicals $R_1$ to $R_3$, which may be identical or different, represent a linear or branched aliphatic radical containing from 1 to 4 carbon atoms, or an aromatic radical such as aryl or alkylaryl. The aliphatic radicals can comprise hetero atoms such as, in particular, oxygen, nitrogen, sulphur or halogens. The aliphatic radicals are chosen, for example, from alkyl, alkoxy and alkylamide radicals, $R_4$ denotes a linear or branched alkyl radical containing from 16 to 30 carbon atoms.

The cationic surfactant is preferably a behenyltrimethylammonium salt (for example chloride).

ii) the radicals $R_1$ and $R_2$, which may be identical or different, represent a linear or branched aliphatic radical containing from 1 to 4 carbon atoms, or an aromatic radical such as aryl or alkylaryl. The aliphatic radicals can comprise hetero atoms such as, in particular, oxygen, nitrogen, sulphur or halogens. The aliphatic radicals are chosen, for example, from alkyl, alkoxy, alkylamide and hydroxyalkyl radicals containing from about 1 to 4 carbon atoms;

$R_3$ and $R_4$, which may be identical or different, denote a linear or branched alkyl radical containing from 12 to 30 carbon atoms, the said radical comprising at least one ester or amide function.

$R_3$ and $R_4$ are chosen in particular from ($C_{12}$-$C_{22}$)alkylamido($C_2$-$C_6$)alkyl and ($C_{12}$-$C_{22}$)alkylacetate radicals.

The cationic surfactant is preferably a stearamidopropyldimethyl(myristyl acetate)ammonium salt (for example chloride);

B)—the quaternary ammonium salts of imidazolinium, such as, for example, that of formula (XXIII) below:

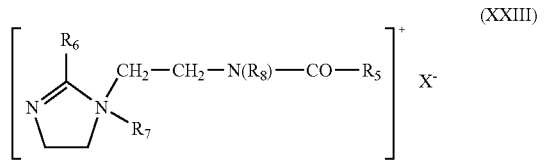

(XXIII)

in which $R_5$ represents an alkenyl or alkyl radical Containing from 8 to 30 carbon atoms, for example fatty acid derivatives of tallow, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical, and $X^-$ is an anion chosen from the group of halides, phosphates, acetates, lactates, alkyl sulphates, alkyl sulphonates or alkylaryl sulphonates. $R_5$ and $R_6$ preferably denote a mixture of alkenyl or alkyl radicals containing from 12 to 21 carbon atoms, such as, for example, fatty acid derivatives of tallow, $R_7$ denotes methyl and $R_8$ denotes hydrogen. Such a product is, for example, Quaternium-27 (CTFA 1997) or Quaternium-83 (CTFA 1997), which are sold under the names "Rewoquat®" W75, W90, W75PG and W75HPG by the company Witco;

C)—the diquaternary ammonium salts of formula (XXIV):

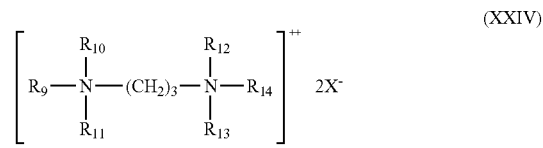

(XXIV)

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen and an alkyl radical containing from 1 to 4 carbon atoms, and $X^-$ is an anion chosen from the group of halides, acetates, phosphates, nitrates and methyl sulphates. Such diquaternary ammonium salts in particular comprise propanetallowdiammonium dichloride;

D)—the quaternary ammonium salts containing at least one ester function, of formula (XXV) below:

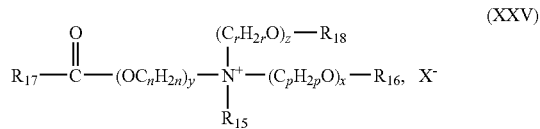

(XXV)

in which:

$R_{15}$ is chosen from $C_1$-$C_6$ alkyl radicals and $C_1$-$C_6$ hydroxyalkyl or dihydroxyalkyl radicals;

$R_{16}$ is chosen from:

a radical

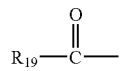

linear or branched, saturated or unsaturated $C_1$-$C_{22}$ hydrocarbon-based radicals $R_{20}$, a hydrogen atom, $R_{18}$ is chosen from:

a radical

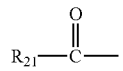

linear or branched, saturated or unsaturated $C_1$-$C_6$ hydrocarbon-based radicals $R_{22}$, a hydrogen atom, $R_{17}$, $R_{19}$ and $R_{21}$, which may be identical or different, are chosen from linear or branched, saturated or unsaturated $C_7$-$C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or mineral anion; with the proviso that the sum x+y+z is from 1 to 15, that when x is 0, then $R_{16}$ denotes $R_{20}$ and that when z is 0, then $R_{18}$ denotes $R_{22}$.

Use is made more particularly of the ammonium salts of formula (XXV) in which:

$R_{15}$ denotes a methyl or ethyl radical, x and y are equal to 1;

z is equal to 0 or 1;

n, p and r are equal to 2;

$R_{16}$ is chosen from:

a radical

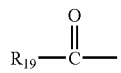

methyl, ethyl or $C_{14}$-$C_{22}$ hydrocarbon-based radicals, a hydrogen atom;

$R_{17}$, $R_{19}$ and $R_{21}$, which may be identical or different, are chosen from linear or branched, saturated or unsaturated $C_7$-$C_{21}$ hydrocarbon-based radicals;

$R_{18}$ is chosen from:

a radical

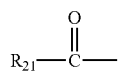

a hydrogen atom.

Such compounds are sold, for example, under the names Dehyguart® by the company Cognis, Stepanquat® by the company Stepan, Noxamium® by the company Ceca, and Rewoquat® WE 18 by the company Rewo-Witco.

Among the quaternary ammonium salts that are preferred are stearamidopropyldimethyl(myristyl acetate)ammonium chloride, sold under the name "Ceraphyl® 70" by the company Van Dyk, and Quaternium-27 or Quaternium-83 sold by the company Witco.

The concentration of active agents in the compositions that are useful in the process of the present invention is between 0.001% and 20% and preferably between 0.01% and 10% relative to the total weight of the composition.

The heating iron that is useful in the context of the invention is a heating iron conventionally used in the hair field. Such an iron, for example a curling iron or a smoothing iron, is well known in the field of hair treatment. For example, irons that are useful for performing the present invention are flat or round irons described in U.S. Pat. Nos. 4,103,145, 4,308,878, 5,983,903, 5,957,140 and 5,494,058.

In the context of the invention, the temperature is greater than 60° C. Preferably, this temperature is between 60° C. and 220° C. Even more preferably, this temperature is between 120 and 200° C.

The iron may be applied to the hair by successive touches or by sliding it along the hair.

It is possible, between the application of the hair composition and the application of the heating iron to the keratin fibres, to include a rest phase. It is also possible to include a rinsing step before applying the iron to the fibres.

The hair composition according to the present invention contains active agents of the type described above, in a medium that is suitable for treating the hair. Such a medium generally consists of water or a mixture of water and at least one organic solvent to dissolve the compounds which would not be sufficiently soluble in water. As organic solvent, mention maybe made, for example, of $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvents are preferably present in proportions preferably of between 1% and 40% by weight approximately relative to the total weight of the dye composition, and even more preferably between 5% and 30% by weight approximately.

The composition may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Preferably, the compositions used according to the invention contain a thickening polymer. According to one particularly preferred embodiment, the thickening polymer is a superabsorbent polymer.

The above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the treatment composition in accordance with the invention are not, or are not substantially, adversely affected by the envisaged addition(s).

The pH of the composition is generally between about 3 and 12 and preferably between about 5 and 11. It may be adjusted to the desired value using acidifying or basifying agents usually used in the dyeing of keratin fibres, or alternatively using standard buffer systems.

Among the acidifying agents that may be mentioned, for example, are mineral or organic acids such as hydrochloric acid, orthophosphoric acid, sulphuric acid, carboxylic acids such as acetic acid, tartaric acid, citric acid and lactic acid, and sulphonic acids.

Among the basifying agents that may be mentioned, for example, are aqueous ammonia, alkaline carbonates, alkanolamines such as mono-, di- and triethanolamine and derivatives thereof, sodium hydroxide, potassium hydroxide and the compounds of formula (II) below.

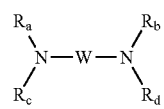

(II)

in which W is a propylene residue which is unsubstituted or substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

The composition applied to the keratin fibres may be in various forms, such as in the form of liquids, creams or gels or in any other form that is suitable for dyeing keratin fibres, and especially human hair.

A subject of the invention is also a composition containing at least one superabsorbent polymer and at least one active agent chosen from hair dyes, oxidizing agents and cationic conditioners. According to one particular embodiment, the composition for dyeing keratin fibres comprises, in a medium that is suitable for dyeing keratin fibres, at least one superabsorbent polymer and at least one hair dye, and optionally an oxidizing agent or a cationic conditioner, the dye, the oxidizing agent or the conditioner being as defined above.

For the purposes of the present invention, the term "superabsorbent polymer" means any polymer having a free swelling capacity of greater than 20 and preferably greater than 30, at room temperature (25° C.) and at atmospheric pressure.

This value, which is equivalent to the amount of fluid absorbed per gram of polymer, is determined by dispersing 0.5 g of polymer in 150 g of 1% sodium chloride solution, waiting 20 minutes, filtering the solution not absorbed through a 150 μm filter for 20 minutes and weighing the water not absorbed.

Examples of superabsorbent polymers that may be mentioned include those described in U.S. Pat. Nos. 3,926,891, 4,190,562, 4,293,609, 4,424,247 and 4,535,098.

The superabsorbent polymers are preferably crosslinked polyacrylates.

Particular examples that may be mentioned are the products sold by the company Technical Absorbents under the reference Oasis Fibre 6 mm Superabsorbent Type 101.

Preferably, the concentration of superabsorbent polymer is between 0.05 and 20% and more preferably between 0.1% and 10% relative to the total weight of the composition.

The examples that follow illustrate the invention without, however, limiting the scope.

EXAMPLES

The following hair compositions are prepared:

| Composition A | |
|---|---|
| Oasis Fibre 6 mm Superabsorbent Type 101 | 3.23 g |
| Basic Red 51 dye | 0.073 g |
| Water | qs 100 g |

| Composition B | |
|---|---|
| Oasis Fibre 6 mm Superabsorbent Type 101 | 2.78 g |
| Basic Red 51 dye | 0.063 g |
| Cyclopentasiloxane | 6.9 g |
| Shorea Robusta Seed Butter | $6.9 \times 10^{-3}$ g |
| Fragrance | 0.03 g |
| Cyclopentasiloxane and Dimethiconol | 6.945 g |
| Elaeis Guineensis | $6.9 \times 10^{-3}$ g |
| Water | qs 100 g |

| Composition C | |
|---|---|
| Oasis Fibre 6 mm Superabsorbent Type 101 | 2.44 g |
| Basic Red 51 dye | 0.055 g |
| Cyclopentasiloxane | 12.12 g |
| Shorea Robusta Seed Butter | 0.012 g |
| Fragrance | 0.049 g |
| Cyclopentasiloxane and Dimethiconol | 12.195 g |

| -continued | |
|---|---|
| Composition C | |
| Elaeis Guineensis | 0.012 g |
| water | qs 100 g |

The compositions are applied to two pairs of permanent-waved (BP) and non-permanent-waved (BN) locks. One of the locks of each of the pairs is treated with a heating iron at a temperature of 180° C. by sliding it along the fibres.

After rinsing, washing with shampoo, rinsing and drying, each lock is evaluated before and after dyeing, in the L*a*b* system, using a Minolta® CM 2002 spectrophotometer (illuminant D65).

In the L*a*b* system, the three parameters denote, respectively, the lightness (L*), the hue (a*) and the saturation (b*). According to this system, the higher the value of L, the paler or weaker the colour. Conversely, the lower the value of L, the darker or stronger the colour. a* and b* indicate two colour axes; a* indicates the green/red colour axis and b* indicates the blue/yellow colour axis.

The locks treated with the iron are more strongly coloured than those not treated with the iron.

| Colorimetric results of the locks | | | | | |
|---|---|---|---|---|---|
| Composition | Iron | BN/BP | L* | a* | b* |
| A | with | BP | 35.64 | 30.05 | 1.22 |
| | | BN | 36.23 | 32.21 | 2.06 |
| | without | BP | 48.17 | 14.1 | 5.51 |
| | | BN | 45.65 | 16.7 | 4.56 |
| B | with | BP | 36.95 | 29.55 | 1.69 |
| | | BN | 33.87 | 28.04 | 2.69 |
| | without | BP | 51.58 | 12.97 | 6.90 |
| | | BN | 46.92 | 9.4 | 6.74 |
| C | with | BP | 41.97 | 22.85 | 3.34 |
| | | BN | 42.46 | 24.38 | 3.30 |
| | without | BP | 48.54 | 11.76 | 6.95 |
| | | BN | 44.2 | 10.70 | 6.96 |

In all cases, the value L* with treatment with the iron is lower than that without treatment with the iron. The hues are thus stronger with the treatment according to the present invention.

It is also observed that the hues obtained are more chromatic with the treatment with the iron, the chromaticity being calculated by $(a^{*2}+b^{*2})^{1/2}$.

The invention claimed is:

1. A process for treating keratin fibers, comprising:
   applying to the keratin fibers at least one hair composition comprising, in a medium that is suitable for dyeing fibers, at least one active agent chosen from:
   at least one direct dye;
   at least one oxidation base;
   at least one coupler; and
   at least one oxidizing agent, and
   then heating the fibers coated with the hair composition, using a heating iron whose temperature is greater than or equal to 60° C.

2. The process according to claim 1, wherein the temperature of the heating iron ranges from 60 to 220° C.

3. The process according to claim 2, wherein the temperature of the heating iron ranges from 120 to 200° C.

4. The process according to claim 1, wherein the at least one oxidation base is chosen from para-phenylenediamines, bis(phenyl)alkylened iamines, para-aminophenols, ortho-aminophenols, heterocyclic bases, and the addition salts thereof.

5. The process according to claim 1, wherein the at least one coupler is chosen from meta-phenylenediamines, meta-aminophenols, meta-diphenols, naphthalene-based and heterocyclic couplers, and the addition salts thereof.

6. The process according to claim 1, wherein the at least one direct dye is chosen from nitrobenezene dyes, azo direct dyes, methine direct dyes, and is optionally of a nonionic, anionic or cationic nature.

7. The process according to claim 1, wherein the at least one oxidizing agent is chosen from hydrogen peroxide, urea peroxide, alkali metal bromates, persalts, peracids and 2-electron or 4-electron oxidase enzymes.

8. The process according to claim 1, wherein the at least one hair composition further comprises at least one cationic conditioner chosen from cationic polymers, cationic proteins, cationic protein hydrolysates and cationic surfactants, and mixtures thereof.

9. The process according to claim 8, wherein the cationic polymers are chosen from those containing units comprising primary, secondary, tertiary and/or quaternary amine groups, which either may form part of the main polymer chain or may be borne by a side substituent directly attached thereto.

10. The process according to claim 8, wherein the cationic polymers are chosen from cationic cyclopolymers, cationic polysaccharides and quaternary polymers of vinylpyrrolidone and of vinylimidazole, and mixtures thereof.

11. The process according to claim 10, wherein the cationic cyclopolymers are chosen from diallyldimethylammonium chloride homopolymers and copolymers of diallyldimethylammonium chloride and of acrylamide.

12. The process according to claim 10, wherein the cationic polysaccharides are chosen from hydroxyethylcelluloses that have reacted with an epoxide substituted with a trimethylammonium group.

13. The process according to claim 10, wherein the cationic polysaccharides are chosen from guar gums modified with a 2,3-epoxypropyltrimethylammonium salt.

14. The process according to claim 8, wherein the cationic surfactants are chosen from:

A) the quaternary ammonium salts of general formula (XXII) below:

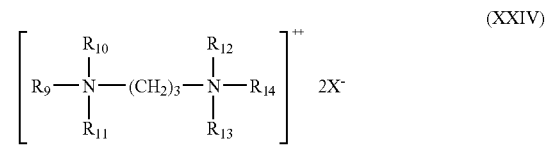

wherein:
X$^-$ is an anion chosen from halides, ($C_2$-$C_6$)alkyl sulphates, phosphates, alkyl or alkylaryl sulphonates, and anions derived from organic acids, and i) the radicals $R_1$ to $R_3$, in which may be identical or different, are chosen from linear or branched aliphatic radicals containing from 1 to 4 carbon atoms, and from aromatic radicals, optionally comprising hetero atoms; and $R_4$ is a linear or branched alkyl radical containing from 16 to 30 carbon atoms;

ii) the radicals $R_1$, and $R_2$, which may be identical or different, are chosen from linear or branched aliphatic radicals containing from 1 to 4 carbon atoms, and from aromatic radicals, optionally comprising hetero atoms; and iii) the radicals $R_3$ and $R_4$, which may be identical or different, are chosen from linear or branched $C_{12}$ to $C_{30}$ alkyl radicals, said radicals comprising at least one ester or amide function;

B) the quaternary ammonium salts of imidazolinium;
C) the diquaternary ammonium salts of formula (XXIV):

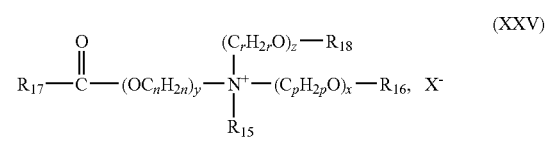

wherein:
$R_5$ is an aliphatic radical containing from 16 to 30 carbon atoms,
$R_{10}$, $R_{11}$, $R_{12}$, $R_{13}$ and $R_{14}$, which may be identical or different, are each chosen from hydrogen and $C_1$ to $C_4$ alkyl radicals,
and X$^-$ is an anion chosen from halides, acetates, phosphates, nitrates, and methyl sulphates;

D) the quaternary ammonium salts containing at least one ester function, of formula (XXV) below:

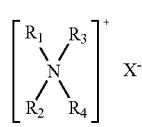

wherein:
$R_{15}$ is chosen from $C_1$-$C_6$ alkyl radicals and $C_1$-$C_6$ hydroxyalkyl or dihydroxyalkyl radicals;
$R_{16}$ is chosen from:
radical

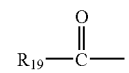

a linear or branched, saturated or unsaturated $C_1$-$C_{22}$ hydrocarbon-based radical $R_{20}$,
a hydrogen atom,
$R_{18}$ is chosen from:
a radical

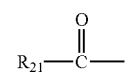

a linear or branched, saturated or unsaturated $C_1$-$C_6$ hydrocarbon-based radical $R_{22}$, and
a hydrogen atom,
$R_{17}$, $R_{19}$ and $R_{22}$, which may be identical or different, are each chosen from linear or branched, saturated or unsaturated $C_7$-$C_{22}$ hydrocarbon-based radicals;
n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or mineral anion;

with the provisos that the sum x+y+Z is from 1 to 15, that when x is 0, then $R_{16}$ denotes $R_{20}$ and that when z is 0, then $R_{18}$ denotes $R_{22}$.

15. The process according to claim 14, wherein the quaternary ammonium salts of imidazolinium are of formula Q(XIII) below:

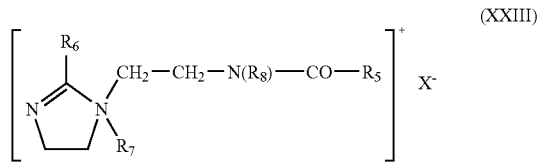
(XXIII)

wherein:

$R_5$ is an alkenyl or alkyl radical containing from 8 to 30 carbon atoms;

$R_6$ is a hydrogen atom, a $C_1$-$C_4$ alkyl radical or a $C_8$ to $C_{30}$ alkenyl or alkyl radical;

$R_7$ is a $C_1$-$C_4$ alkyl radical;

$R_8$ is a hydrogen atom or a $C_1$-C alkyl radical; and $X^-$ is an anion chosen from halides, phosphates, acetates, lactates, alkyl sulphates, alkyl sulphonates, and alkylaryl sulphonates.

16. The process according to claim 1, wherein the concentration of the at least one active agent in the at least one hair composition ranges from 0.001% to 20% by weight of the composition.

17. The process according to claim 1, wherein the at least one hair composition further comprises at least one superabsorbent polymer.

18. The process according to claim 1, wherein there is a waiting period between applying the at least one hair composition and the heating of the keratin fibers.

19. The process according to claim 1, wherein the hair fibers are rinsed between applying the at least one hair composition and the heating of the keratin fibers.

* * * * *

UNITED STATES PATENT AND TRADEMARK OFFICE
CERTIFICATE OF CORRECTION

| | |
|---|---|
| PATENT NO. | : 7,608,115 B2 |
| APPLICATION NO. | : 10/556044 |
| DATED | : October 27, 2009 |
| INVENTOR(S) | : Roland De La Mettrie |

It is certified that error appears in the above-identified patent and that said Letters Patent is hereby corrected as shown below:

On the title page, item (57), line 8, "least-one" should read --least one--.

In claim 4, column 21, line 1, "bis(phenyl)alkylened iamines," should read --bis(phenyl)alkylenediamines,--.

In claim 14, column 21, line 66, "$R_1$," should read --$R_1$--.

In claim 14, column 23, line 5, "x+y+Z" should read --x+y+z--.

In claim 15, column 23, line 10, "Q(XIII)" should read --(XXIII)--.

In claim 15, column 24, line 3, "$C_1$ -$C_4$" should read --$C_1$-$C_4$--.

In claim 15, column 24, line 4, "$C_1$ -C" should read --$C_1$-$C_4$--.

Signed and Sealed this

Twenty-second Day of December, 2009

David J. Kappos
*Director of the United States Patent and Trademark Office*